United States Patent [19]

Gambaro

[11] 4,280,518
[45] Jul. 28, 1981

[54] TOOTH CLEANING IMPLEMENT

[76] Inventor: Susan M. Gambaro, 4811 Densmore St., Encino, Calif. 91436

[21] Appl. No.: 28,130

[22] Filed: Apr. 9, 1979

[51] Int. Cl.³ .......................................... A61C 15/00
[52] U.S. Cl. ................................................ 132/93
[58] Field of Search .................. 132/93, 89, 91, 92 R

[56] References Cited

U.S. PATENT DOCUMENTS

| | | | |
|---|---|---|---|
| 1,890,788 | 12/1932 | Landis | 132/91 |
| 2,113,439 | 4/1938 | Bean | 132/92 R |
| 2,187,076 | 1/1940 | Erickson | 132/84 R |
| 2,444,638 | 7/1948 | Dobbins | 132/92 R |
| 3,050,072 | 8/1962 | Diener | 132/93 |
| 3,896,523 | 7/1975 | Spatz | 132/88.7 |
| 4,056,111 | 11/1977 | Mantelel | 132/11 A |
| 4,165,755 | 8/1979 | Cassai | 132/88.7 |

*Primary Examiner*—G. E. McNeill
*Attorney, Agent, or Firm*—Jack C. Munro

[57] ABSTRACT

An implement to facilitate the cleaning of teeth which takes the form of an elongated member which has at one end thereof tautly stretched thereacross a strand of dental floss. The opposite end of the elongated member is attached to a brush-like member which is to facilitate the cleaning of not only teeth, but dental bridges. The brush-like member can be constructed to be integral with the elongated member or can be constructed to be removably secured thereto.

2 Claims, 4 Drawing Figures

TOOTH CLEANING IMPLEMENT

BACKGROUND OF THE INVENTION

It has been well known in the past to provide some form of an implement to facilitate the removing of food particles from between a person's teeth. Such items have been frequently referred to as a toothpick and generally take the form of an elongated pointed tool which is adapted to be inserted between a person's teeth and moved in order to dislodge any food particles and plaque located between the teeth.

It has been further found to be desirable to not only employ the use of a pointed instrument, but also to employ the use of a strand of thread which is commonly referred to as dental floss. A segment of the dental floss is to be stretched taut and then inserted between the person's teeth and moved back and forth in order to effect removal of any lodged food particles and plaque.

For a person who wears a dental bridge, the use of dental floss and toothpicks may be difficult. A small brush has been found to be far more desirable for bridge wearers to remove lodged food particles and plaque. However, prior to this invention, there has not been known to include the use of a brush within a portable and disposable tooth cleaning implement.

SUMMARY OF THE INVENTION

The tooth cleaning implement of this invention takes the form of an elongated, preferably plastic, member which has a fore end and an aft end. The fore end is bifurcated providing a pair of spaced-apart leg members. A strand of dental floss is to be secured to the free ends of each of the leg members and stretched taut between. The aft end of the elongated member is connected to a brush-like device which may take the form of a bristle-type brush or may take the form of a bristle simulating device such as being constructed of a plurality of closely spaced-apart annular discs which are inherently bendable. The discs are to deform so as to simulate the action of a bristle-type brush. In a second embodiment of this invention, the aft end of the elongated member may be removable secured to a conventional, small sized bristle brush. The attachment between the elongated member and the bristle brush is to be by inserting of the elongated member into a sleeve which is formed as part of the bristle brush.

DETAILED DESCRIPTION OF THE SHOWN EMBODIMENTS

Figure 1:
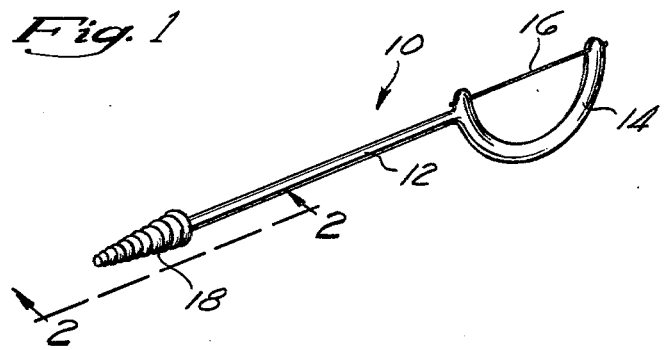
FIG. 1 is an isometric view of the first embodiment of the tooth cleaning implement of this invention.
Figure 2:
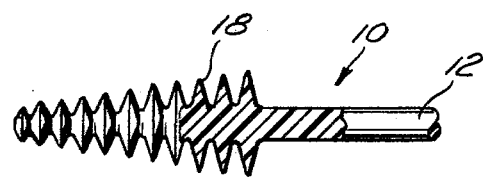
FIG. 2 is an enlarged side view, partly in cross-section, of the tooth cleaning implement of FIG. 1 taken along line 2—2 of FIG. 1.

Referring particularly to the drawing, there is shown in FIGS. 1 and 2 of the first embodiment of a tooth cleaning implement 10 of this invention. The implement 10 includes an elongated body member 12 which is usually to be constructed of plastic or other similar type of rigid but yet slightly bendable material. Wood could also be employed. The fore end of the member 12 is formed into a bifurcated section resembling a "C" or "U"-shaped section 14. The outermost ends of the spaced apart leg members of the "C"-shaped section 14 has attached thereto a strand 16 of dental floss. This strand of dental floss 16 is attached so as to be taut. The purpose of the dental floss 16 is to be usable between a person's teeth in the normal conventional manner.

The aft end of the elongated member has integrally attached thereto a series of closely spaced annular discs 18. It is to be noted that the diameter of each of the discs 18 varies so that the outermost disc 18 is substantially smaller in diameter than the innermost disc 18. This outwardly tapering is desirable to facilitate insertion of the disc 18 between crevices within a persons teeth and bridge work. It is to be noted that disc 18 will be constructed of a plastic material and of a type of plastic material that will facilitate bending or flexing of the disc 18 so as to essentially resemble a conventional bristle type brush.

Figure 3:
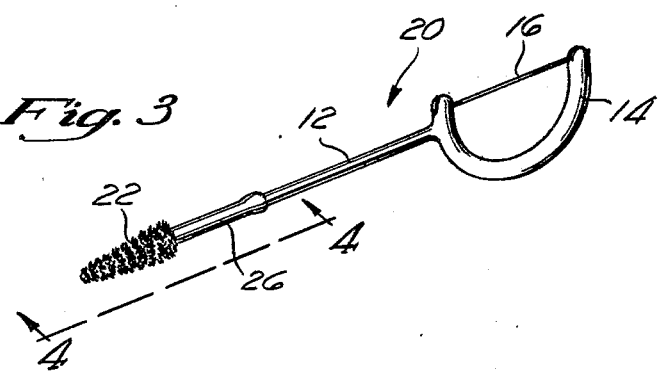
FIG. 3 is an isometric view similar to FIG. 1, but of a second embodiment of this invention which employs the use of a bristle-type of brush attached to the aft end of the tooth cleaning implement.
Figure 4:
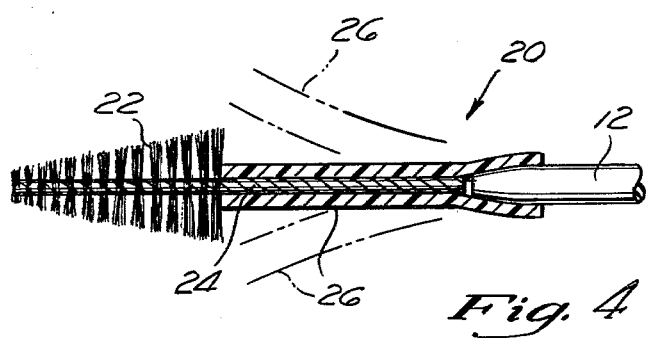
FIG. 4 is a view similar to FIG. 2, but taken along line 4—4 of FIG. 3.

Referring particularly to FIGS. 3 and 4, there is a second embodiment 20 of this invention wherein like numerals have been employed to refer to like parts. The only difference between the embodiment within FIGS. 3 and 4 and the embodiments of FIGS. 1 and 2 is that the brush-like member 22 is a conventional bristle type brush which is tapered to a point. The brush 22 includes bristles which are wound onto a wire rod 24. This wire rod 24 is fixedly secured within a plastic sleeve 26. The outer end of the plastic sleeve 26 is hollow and is adapted to be inserted over the outer end of the elongated member 12 as is shown in FIG. 4. This then permits the structure of FIGS. 3 and 4 to be employed as an implement which includes dental floss and has a sharp pointed end which can be used as a toothpick which then can be further employed to include a brush attachment.

What is claimed is:

1. An implement to facilitate the cleaning of teeth comprising:

an elongated member having a fore end and an aft end, said elongated member having a first longitudinal center axis, a strand of stretched taut dental floss being connected to said fore end, said fore end taking the form of a bifurcated member having a pair of spaced-apart leg members, said dental floss to be stretched between and attached to said leg members, said dental floss being parallel to said first longitudinal center axis;

a brush-like member attached to said aft end, said brush-like member having a cross-sectional size greater than the cross-sectional size of said elongated member, said brush-like member being tapered in its longitudinal direction so that the outermost end of said brush-like member essentially comes to a point, said brush-like member being attached to a resilient sleeve, said aft end of said elongated member to be inserted within said sleeve and said sleeve deforming about said elongated member thereby tightly securing said elongated member to said brush-like member, said brush-like member having a second longitudinal center axis, said second longitudinal center axis coinciding with said first longitudinal center axis.

2. The implement as defined in claim 1 wherein: said brush-like member taking the form of a plurality of spaced-apart flexible annular discs.

* * * * *